(12) United States Patent
Hoffmann

(10) Patent No.: US 8,523,953 B2
(45) Date of Patent: Sep. 3, 2013

(54) USE OF AN AMINE AND/OR A QUATERNARY AMMONIUM COMPOUND FOR PROTECTING COLOUR OF ARTIFICIALLY COLOURED HAIR WITH RESPECT TO THE WASHING AND PROCESS THEREFORE

(75) Inventor: Martin Hoffmann, Zwingenberg (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/636,504

(22) PCT Filed: Apr. 19, 2011

(86) PCT No.: PCT/EP2011/056263
§ 371 (c)(1),
(2), (4) Date: Sep. 21, 2012

(87) PCT Pub. No.: WO2011/134848
PCT Pub. Date: Nov. 3, 2011

(65) Prior Publication Data
US 2013/0037045 A1    Feb. 14, 2013

(30) Foreign Application Priority Data
Apr. 29, 2010  (EP) ..................................... 10004514

(51) Int. Cl.
*C11D 3/00*    (2006.01)
*A61K 8/00*    (2006.01)

(52) U.S. Cl.
USPC ............ 8/137; 8/406; 8/442; 8/606; 424/401; 424/70.13

(58) Field of Classification Search
USPC .................... 8/137, 406, 442, 606; 424/401, 424/70.13
See application file for complete search history.

(56) References Cited

FOREIGN PATENT DOCUMENTS

| | | |
|---|---|---|
| DE | 100 55 947 A1 | 5/2002 |
| EP | 1 366 755 A1 | 12/2003 |
| EP | 1 547 574 A1 | 6/2005 |
| EP | 1547574 A1 * | 6/2005 |
| WO | 2007/146672 A2 | 12/2007 |
| WO | 2008/070566 A1 | 6/2008 |

OTHER PUBLICATIONS

STIC Search Report dated Mar. 15, 2013.*
International Search Report Dated Jan. 19, 2012, Mailed Feb. 3, 2012.

* cited by examiner

*Primary Examiner* — Eisa Elhilo
(74) *Attorney, Agent, or Firm* — Norris McLaughlin & Marcus P.A.

(57) ABSTRACT

The present invention relates to the use of amine and quaternary ammonium compounds for protecting hair color of artificially colored hair with respect to the washing, according to general structure $R_1$-A-$R_2$—B Wherein $R_1$, A, $R_2$ and B are defined in the claims and in the specification or

—$R_2$-A-$R_1$

Wherein $R_1$, A, $R_2$ have the above meaning.

14 Claims, No Drawings

USE OF AN AMINE AND/OR A QUATERNARY AMMONIUM COMPOUND FOR PROTECTING COLOUR OF ARTIFICIALLY COLOURED HAIR WITH RESPECT TO THE WASHING AND PROCESS THEREFORE

This application is a 371 application of PCT/EP2011/0566263 filed Apr. 19, 2011, which claims foreign priority benefit under 35 U.S.C. §119 of European Application No. 10004514.4 filed Apr. 29, 2010.

The present invention relates to the use of some amine and quaternary ammonium compounds for protecting hair colour of artificially coloured hair with respect to the washing.

Conditioning compositions for hair have been known for ages. Various types of conditioners are available on the market and new ones are being introduced almost every day. It is also known that after hair colouring, a conditioning composition is applied onto hair in order to give rich conditioning. It is also known that conditioners remove colour form hair especially from hair surface. Therefore, there is a need for new conditioners which first of all does not wash out hair colour itself and also does have a kind of sealing effect so that in subsequent hair washes minimum level of colour is washed out.

It is also known that hair conditioners are usually emulsion types, especially the ones rinsed off after certain processing time, and comprise fatty alcohols and cationic and cationizable compounds. However, protective effect of the compounds claimed with this invention has never been reported up until now.

The inventor of the present invention has surprisingly found out that certain types of amine and or quaternary ammonium compounds are very effective in protecting colour of artificially coloured hair with respect to the washing.

Accordingly, the first object of the present invention is the use of a compound according to general structure

wherein $R_1$ is a saturated or unsaturated, straight or branched alkyl group with 8 to 24 C atoms, $R_2$ is a straight or branched alkyl group with 1 to 4 C atoms, A is a group selected from O,

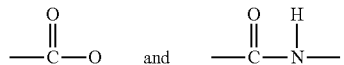

and B is selected from

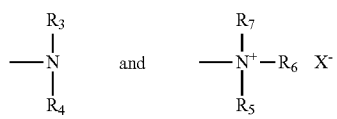

$R_3$ and $R_4$ are the same or different, H or an alkyl with 1 to 4 C atoms, hydroxyl alkyl with 1 to 4 C atoms and dihydroxyl alkyl with 2 to 4 C atoms, $R_5$, and $R_6$ are the same or different, an alkyl with 1 to 4 C atoms, hydroxyl alkyl with 1 to 4 C atoms and dihydroxyl alkyl with 2 to 4 C atoms, $R_7$ is an alkyl with 1 to 4 C atoms, hydroxyl alkyl with 1 to 4 C atoms or dihydroxyl alkyl with 2 to 4 C atoms and

wherein $R_1$, A and $R_2$ have the above meaning and X is an anion such as chloride, bromide, and methosulfate, for protecting colour of artificially coloured hair with respect to the washing.

Second object of the present invention is the use of a compound according to general structure given above as an agent for protecting colour of artificially coloured hair with respect to the washing in compositions applied immediately after artificially colouring hair.

Third object of the present invention is method of protecting colour of artificially coloured hair with respect to washing wherein a composition is applied onto artificially coloured hair comprising at least one compound according to general structure given above.

Still further object of the present invention is process of protecting colour of artificially coloured hair with respect to washing wherein hair is coloured with a composition comprising at least one oxidative dye precursor and/or direct dye and immediately after rinsing of the said dying composition, a composition is applied comprising at least one compound according to general structure above as a protecting agent.

Still further object of the present invention method of protecting colour of artificially coloured hair with respect to washing wherein a composition is applied onto already coloured comprising at least one compound according to general structure given above and processed on hair up to 30 min and rinsed off from hair.

Still further object of the present invention is process of protecting colour of artificially coloured hair with respect to washing wherein hair is coloured with a composition comprising at least one oxidative dye precursor and/or direct dye and after rinsing of the said dying composition, a composition is applied comprising at least one compound according to general structure above as a protecting agent and processed on hair up to 30 min and rinsed off from hair.

Still further object of the present invention is a kit for protecting colour of artificially coloured hair which comprises one or more separately packed compositions wherein at least one of them comprises a compound according to general structure given above as an agent for protecting colour of artificially coloured hair with respect to the washing.

Compositions of the present invention comprising above given agent for protecting colour of artificially coloured hair are suitable for either rinse off or leave in applications, wherein rinse off application is especially used and preferred. Although this, still further object of the present invention is process for protecting colour of artificially coloured hair with respect to the washing wherein wherein a composition comprising at least one compound according to general structure given above as an agent for protecting colour of artificially coloured hair with respect to the washing and not rinsed off.

Compositions of the present invention comprise at least one compound according to above given general structure. In the preferred embodiment of the present invention, $R_1$ is saturated or unsaturated, straight or branched alkyl group with 10 to 24 C atoms, more preferably 12 to 22 C atoms and $R_2$ is straight or branched alkyl group with 1 to 4 C atoms which may be substituted and preferably ethyl or hydroxyl ethyl, A, B, $R_3$ to $R_7$ are same as above.

Non-limiting suitable examples are stearoxypropyl amine, palmitoxypropyl amine, stearoxypropyldimethyl amine, stearoxypropyldiethyl amine, stearoxyethylyldimethyl amine, stearoxyethyl amine, myristoxypropyl amine, myristoxypropyldimethyl amine, stearoxypropyl trimethyl ammonium chloride, palmitoxypropyl trimethyl ammonium chloride, stearoxypropyl trimethyl ammonium chloride, stearoxypropyltriethyl ammonium chloride, stearoxyethylyltrimethyl ammonium chloride, stearoxyethyl trimethyl ammonium chloride, myristoxypropyl trimethyl ammonium chloride and myristoxypropyltrimethyl ammonium chloride. Preferred are the ones with palmit and stear derived alkyl groups and most preferred are the ones with stear group such as stearoxypropyldimethyl amine.

Concentration of at least one compound according to above given general structure is in the range of 0.01 to 20%, preferably 0.02 to 15%, more preferably 0.05 to 10% and most preferably 0.1 to 7.5% and in particular 0.25 to 5% by weight calculated to total composition.

Compositions comprising at least one compound according to above given general structure can be in various forms such as solution, emulsion, cleansing composition and conditioning composition. These compositions may be confectioned in a non-aerosol and/or an aerosol packaging component. In case aerosol packaging is preferred, an appropriate propellant must be used in order to pressurize the can for effective release of its content. The suitable propellant gasses are carbondioxide, dimethylether and alkanes such as butane, propane, isobutane or their mixtures. Emulsion types are preferred.

The compositions, preferably emulsion type of compositions, comprise additionally at least one fatty alcohol of the following formula $$R_{30}\text{—OH}$$

where $R_{30}$ is a saturated or unsaturated, branched or non-branched fatty acyl chain with 8-24 C atoms. Concentration of fatty alcohols is usually less than 25%, preferably in the range of 1 to 20%, more preferably 2 to 12.5% and most preferably 2 to 10% by weight, calculated to total composition. Typical examples to the most useful fatty alcohols are myristyl alcohol, palmityl alcohol, cetyl alcohol, stearyl alcohol, behenyl alcohol and their mixtures. As a mixed fatty alcohol, the mostly used one is the cetearyl alcohol as well preferred in the compositions of the present invention.

The compositions, preferably emulsion type of compositions, comprise additionally at least one surfactant selected from anionic, amphoteric, nonionic and cationic ones especially as an emulsifier. Preferred are nonionic and cationic ones.

Preferred cationic ones are comprised in addition to ones give above as a protecting agent. Preferred are according to the general formula

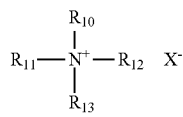

where $R_{10}$ is a saturated or unsaturated, branched or non-branched alkyl chain with 8-24 C atoms and $R_{11}$ is unsaturated or saturated, branched or non-branched alkyl chain with 1-24 C atoms and $R_{12}$ and $R_{13}$ are lower alkyl chain with 1 to 4 carbon atoms which may be substituted with one or more hydroxyl groups, and X is anion such as chloride, bromide, methosulfate.

Typical examples of those ingredients are cetyltrimethyl ammonium chloride, steartrimonium chloride, behentrimonium chloride, myristyltrimethyl ammonium chloride, distearyldimethyl ammonium chloride, and dibehenyldimethyl ammonium chloride. The others known in the textbooks are included herewith by reference.

Nonionic surfactants especially suited as emulsifiers are ethoxylated fatty alcohols and alkyl polyglucosides.

Preferred ethoxylated fatty alcohols are with 10 to 22 C atoms in its alkyl chain and preferably comprises at a concentration of 0.5 to 10%, more preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Suitable alkyl polyglucosides are of the general formula $$R_{17}\text{—O—}(R_{18}O)_n\text{—}Z_x,$$

wherein $R_{17}$ is an alkyl group with 8 to 18 carbon atoms, $R_{18}$ is an ethylene or propylene group, Z is a saccharide group with 5 to 6 carbon atoms, n is a number from 0 to 10 and x is a number between 1 and 5.

Further nonionic surfactant components are, for example, long-chain fatty acid mono- and dialkanolamides, such as coco fatty acid monoethanolamide and myristic fatty acid monoethanolamide, which can also be used as emulsifier.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Emulsifiers are preferably comprised at a concentration of 0.5 to 15%, more preferably 0.5 to 10% by weight, calculated to total composition.

The composition of the present invention can comprise additionally other hair-conditioning agents in any type of composition. Conditioning agents can be selected from oily substances, non-ionic substances, other cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, natural oils such as olive oil, almond oil, avocado oil, wheatgerm oil, ricinus oil and the synthetic oils, such as mineral oil.

Compositions of the present invention can comprise at least one arylated silicone and/or at least one fatty acid fatty alcohol ester as an oily conditioning agent. Non-limiting suitable arylated silicones are phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane.

Non-limiting suitable examples to fatty acid fatty alcohol esters are isopropyl myristate, palmitate, stearate and isostearate, ° leyl oleate, isocetyl stearate, hexyl laurate, dibutyl adipate, dioctyl adipate, myristyl myristate and oleyl erucate.

Concentration of one or more oily substances is in the range of 0.01 to 10%, preferably 0.05 to 7.5%, more preferably 0.1 to 5 and most preferably 0.1 to 3% by weight calculated to total composition. The concentrations referred here are total concentration of all oily substances may be present in the composition.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_8CO(OCH_2CH_2)_nOH \text{ or}$$

$$R_8CO(OCH_2CH_2)_nOOCR_9$$

where $R_8$ and $R_9$ are independent from each other saturated, unsaturated or branched or non-branched alkyl chain with 7 to 21 C atoms and n is typically 2-100.

Further conditioning agents are cationic polymers. Suitable cationic polymers are those of best known with their INCI category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87 as well as silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20, silicone quaternium-21 and silicone quaternium-22.

As well those polymers known with their INCI category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic Caesalpinia spinosa gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Typical concentration range for cationic polymers, is 0.01-5% by weight, preferably 0.01-2.5% by weight calculated to the total composition.

Compositions may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Composition of the present invention can preferably comprise at least one polyphenol. With the word polyphenol it is meant that an organic molecule with at least 2 hydroxyl groups in its molecule.

In the preferred from of the invention, at least one polyphenol or mixture of polyhenols is included into compositions of the present invention from a natural plant extract. In principal any natural plant extract rich of polyphenols is suitable within the meaning of the present invention. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", $4^{th}$ Ed. Preferred plant extracts are prepared from *Vitis vinifera, Malus domestica, Camelia sinensis, Juglans regia Ribes Uva-Crispa, Ribes nigrum, Ribes rubrum* and *Punica granatum*. The above mentioned extracts may also be available in the powder form and such are also suitable within the meaning of the present invention.

The polyphenol comprising extracts are included into the compositions of the present invention at a concentration of 0.001 to 10%, preferably 0.005 to 7.5%, more preferably 0.01 to 5% and most preferably 0.05 to 2.5% by weight, calculated to total composition based on dry matter of the extract.

Further in preferred embodiment of the present invention, compositions comprise at least one UV filter and at least one ubichinone of the following formula

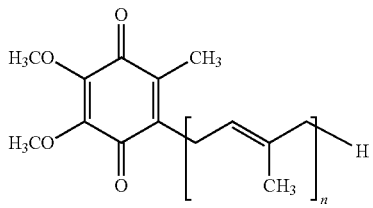

where n is a number between 1 and 10. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Compositions of the present invention preferably comprise at least one UV filter. Principally any substance known as UV filter is suitable for the compositions of the present invention. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof, 3-(4'-methyl benzylidene)-DL-campher, and/or polysilicone-15. Above mentioned UV filters are those oil and water soluble ones for the purpose of protecting hair colour. In other words, anionic and nonionic, oily, UV filters are suitably used in the compositions of the present invention. In the preferred from of the invention the compositions comprise at least one water soluble UV filter and at least one oil soluble one. Further preferred that both UV filters are present at a weight ratio in the range of oil soluble to water soluble UV filter 1:10 to 10:1, preferably 1:5 to 5:1, more preferably 1:3 to 3:1 and most preferably 1:1 in the compositions of the present invention.

The amount of the UV-absorber as a total ranges typically from about 0.01% to 5%, preferably 0.05 to 3%, more preferably from 0.05% to 2.5% and most preferably from 0.1% to 2% by weight, calculated to the total composition.

In another preferred form of the invention, conditioning composition can comprise one or more organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzylalcohol and polypropylene glycols. Concentration of organic solvents should not exceed 10% by weight, preferably in the range of 0.1 to 7.5%, more preferably 0.1 to 5% by weight and most preferably 0.1 to 3% by weight calculated to total composition.

Conditioning composition of the present invention comprises at least one glyceryl ether of the following formula

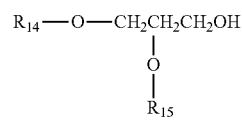

wherein $R_{14}$ is straight or branched, saturated or unsaturated alkyl chain with 4 to 24 C atoms, preferably 4 to 18 and more preferably 4 to 12 C atoms and $R_{15}$ is H, or straight or branched, saturated or unsaturated alkyl chain with 4 to 24 C atoms, preferably 4 to 18 and more preferably 4 to 12 C atoms and most preferably $R_5$ is H, at a concentration of 0.1 to 10%, preferably 0.1 to 5% and more preferably 0.25 to 3% and most preferably 0.5 to 2.5% by weight calculated to total composition.

Suitable unlimited examples are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and their mixtures.

It should be noted that within the disclosure of the present description, glyceryl decyl ether is used as synonym of decyl glycerine. For the other compounds in the above paragraph the same is valid.

Within the meaning of the present invention artificially coloured means that hair is changed its colour by applying a composition comprising at least one oxidative dye precursor and/or at least one direct dye. Within the meaning of the present invention it is not important if oxidizing agent is present in dyeing composition though its presence is preferred especially when colouring composition comprises at least one oxidative dye precursor.

In principal any oxidative dye precursor is suitable within the meaning of present invention. Suitable nonlimiting examples are Some examples are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and 1,2,4-triamino benzene, or the water-soluble salts thereof.

Composition for dyeing hair can also comprise at least one coupling substance. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 5-amino-2-methylphenol, 2-methyl-5-hydroxyethylaminophenol, 2-methyl-5-amino-6-chlorphenol, 2-bis(2-hydroxyethyl)aminotoluene, 2-amino-5-methylphenol, α-naphthol, 4,6-dichlororesorcinol, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxybenzene, 5-amino-2-methoxyphenol, hydroxybenzomorpholine, 1,2,4-trihydroxybenzene, phenylmethylpyrazolone, 3-amino-2,4-dichlorophenol, hydroxyethyl-3,4-methylenedioxyaniline, 2.6-dimethoxy-3,5-dimethylpyridine, 5-amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol and/or or their respective salts.

Hair can as well be coloured with a composition comprising at least one direct dye. Suitable direct dyes are cationic, nitro and anionic ones.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts.

Neutral nitro dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Composition comprising at least one protective agent with above given structure can also be a cleansing composition. Cleansing compositions comprise additionally at least one surfactant selected from anionic, non-ionic and/or amphoteric or zwitterionic surfactants at a concentration range of 5 to 50%, preferably 5 to 40% and more preferably 5 to 30%, and most preferably 5 to 25% by weight, calculated to the total composition. The nonionic surfactants mentioned above as emulsifiers are suitable for cleansing compositions as well.

In an embodiment of the present invention, cleansing composition comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

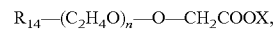

$$R_{14}-(C_2H_4O)_n-O-CH_2COOX,$$

wherein $R_{14}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

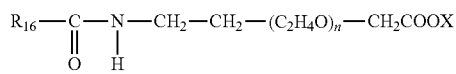

wherein $R_{16}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

An overview of the anionic surfactants used in liquid body cleansing compositions can furthermore be found in the monography of K. Schrader and A. Domsch, "Cosmetology—Theory and Practice", 2005, Verlag für chemische Industrie, Augsburg—Germany, pp. II-8-II-19.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, the cleansing conditioning compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Conditioning compositions of the present invention can comprise moisturizers, chelating agents, preservatives and fragrance. The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The pH of the compositions according to the present invention is suitably between 1.5 and 8 and preferably in the range of 2 to 7, more preferably 2.5 to 6.5 and most preferably 3 to 6.

In principal pH of the compositions can be adjusted with any organic and/or inorganic acids or their mixture. Some of them to mention are phosphoric acid, hydrochloric acid as the inorganic ones and to the organic acids the well known citric acid and lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. It has further been observed that improved conditioning and brightening performance was observed when compositions comprise at the same time at least one hydroxycarboxylic and/or dicarboxylic acids.

The following examples are to illustrate the invention, but not to limit.

EXAMPLE 1

A hair tress weighing approximately 10 g is coloured with the following composition mixing after with an oxidizing composition at a weight ratio of 1:1.

|  | % by weight |
| --- | --- |
| Cetearyl alcohol | 12 |
| Sodium cetearyl sulphate | 3 |
| Cocamide DEA | 5 |
| Oleic acid | 2 |
| Propyleneglycol | 5 |
| Ammonium hydroxide | 8 |
| Sodium sulfite | 0.5 |
| Ascorbic acid | 0.5 |
| p-phenylenediamine | 1 |
| Tetraaminopyrimidine sulphate | 0.5 |
| Resorcinol | 1 |
| Fragrance | q.s |
| Water | to 100 |

The coloured hair was treated with the following composition within the meaning of the present invention.

|  | % by weight |
| --- | --- |
| Cetearyl alcohol | 6 |
| Behentrimonium chloride | 1 |
| Myristyl myristate | 0.5 |
| Stearoxypropyldimethylamine | 1.0 |
| Citric acid | q.s. pH 4.0 |
| Ethanol | 10 |
| Fragrance, preservative | q.s. |
| Water | to 100 |

For comparative purposes, the above composition was also prepared without Stearoxypropyldimethylamine.

In a comparative test lower ΔE value was obtained for the hair tress treated with the composition according to present invention than the tress treated with the comparative composition.

In a subsequent was test with a commercially available cleansing composition, lower ΔE value was obtained for the hair tress treated with the above give inventive composition.

The invention claimed is:

1. A method for protecting color of artificially colored hair with respect to washing, comprising applying to the hair at least one first compound according to general structure

wherein $R_1$ is a saturated or unsaturated, straight or branched alkyl group with 8 to 24 C atoms, $R_2$ is a straight or branched alkyl group with 1 to 4 C atoms, A is a group selected from O,

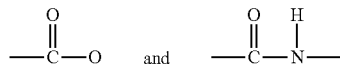

and B is selected from

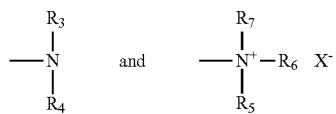

$R_3$ and $R_4$ are the same or different, H or an alkyl with 1 to 4 C atoms, hydroxyl alkyl with 1 to 4 C atoms and dihydroxyl alkyl with 2 to 4 C atoms, $R_5$, and $R_6$ are the same or different, an alkyl with 1 to 4 C atoms, hydroxyl alkyl with 1 to 4 C atoms and dihydroxyl alkyl with 2 to 4 C atoms, $R_7$ is an alkyl with 1 to 4 C atoms, hydroxyl alkyl with 1 to 4 C atoms or di hydroxyl alkyl with 2 to 4 C atoms or

wherein $R_1$, A and $R_2$ have the above meaning and X is an anion selected from the group consisting of chloride, bromide, and methosulfate, for protecting colour of artificially coloured hair with respect to the washing.

2. The method according to claim 1 wherein A is O.

3. The method according to claim 1, comprising, applying the first compound immediately after artificially colouring hair.

4. The method according to claim 1 wherein said first composition is processed on hair up to 30 min and rinsed off from hair.

5. The method according to claim 1, wherein for protecting colour of artificially coloured hair with hair is coloured with a second composition comprising at least one oxidative dye precursor and/or direct dye and immediately after rinsing of the said colouring composition, the first composition is applied as a protecting agent.

6. The method according to claim 5 wherein the second composition comprises at least one oxidative dye precursor and at least one coupling agent.

7. The method according to claim 5 wherein, the second composition comprises at least one direct dye.

8. The method according to claim 5 wherein the first composition is applied immediately after rinsing the second composition and is processed onto hair up to 30 min and rinsed off from hair.

9. The method according to claim 5 wherein the at least one first compound has concentration 0.01 to 20% by weight calculated to total composition.

10. The method according to claim 5 wherein the first composition comprises additionally at least one fatty alcohol according to the formula

where $R_{30}$ is a saturated or unsaturated, branched or non-branched fatty acyl chain with 8-24 C atoms, at a concentration of less than 25% by weight, calculated to total composition.

11. The method according to claim 5 wherein the first composition comprises at least one surfactant selected from anionic, amphoteric, non-ionic and cationic ones, at a concentration of 0.5 to 15% by weight calculated to total composition.

12. The method according to claim 5 wherein the first composition comprises at least one hair conditioning agent selected from silicones, cationic polymers and fatty acid fatty alcohol esters.

13. The method according to claim 5 wherein the first composition comprises at least one UV filter.

14. A kit for protecting colour of artificially coloured hair which comprises one or more separately packed compositions wherein at least one of them comprises a first compound according to claim 1.

* * * * *